United States Patent
Singh et al.

(10) Patent No.: US 10,301,657 B2
(45) Date of Patent: May 28, 2019

(54) AMINO ACID-PRODUCING MICROORGANISMS AND METHODS OF MAKING AND USING

(71) Applicant: MOgene Green Chemicals LLC, St. Louis, MO (US)

(72) Inventors: Abhay Kumar Singh, Chesterfield, MO (US); Himadri Pakrasi, St. Louis, MO (US); Ganesh Murthy Kishore, Creve Coeur, MO (US)

(73) Assignee: MOgene Green Chemicals LLC, St. Louis, MO (US)

( * ) Notice: Subject to any disclaimer, the term of this patent is extended or adjusted under 35 U.S.C. 154(b) by 124 days.

(21) Appl. No.: 15/184,794

(22) Filed: Jun. 16, 2016

(65) Prior Publication Data
US 2016/0369311 A1 Dec. 22, 2016

Related U.S. Application Data

(60) Provisional application No. 62/180,562, filed on Jun. 16, 2015.

(51) Int. Cl.
| | | |
|---|---|---|
| *C12P 13/12* | (2006.01) | |
| *C12N 9/04* | (2006.01) | |
| *C12N 9/10* | (2006.01) | |
| *C12N 15/00* | (2006.01) | |
| *C12N 1/20* | (2006.01) | |
| *C07H 21/04* | (2006.01) | |
| *C12N 9/88* | (2006.01) | |
| *C12N 15/52* | (2006.01) | |

(52) U.S. Cl.
CPC ............ *C12P 13/12* (2013.01); *C12N 9/0006* (2013.01); *C12N 9/1029* (2013.01); *C12N 9/88* (2013.01); *C12N 15/52* (2013.01); *C12Y 101/01027* (2013.01); *C12Y 203/01008* (2013.01); *C12Y 203/01054* (2013.01); *C12Y 401/01001* (2013.01)

(58) Field of Classification Search
None
See application file for complete search history.

(56) References Cited

U.S. PATENT DOCUMENTS 7,192,747 B2 * 3/2007 Ono .................. C12P 13/04
435/106

FOREIGN PATENT DOCUMENTS

WO  WO 2015/058188  * 4/2015

* cited by examiner

*Primary Examiner* — Yong D Pak
(74) *Attorney, Agent, or Firm* — Fish & Richardson P.C.

(57) ABSTRACT

Modified or recombinant microorganisms are provided herein that can be used to produce one or more amino acids, including, for example, methionine or one or more methionine biosynthetic pathway-derived intermediates or one or more methionine-based products.

19 Claims, 4 Drawing Sheets

AMINO ACID-PRODUCING MICROORGANISMS AND METHODS OF MAKING AND USING

CROSS-REFERENCE TO RELATED APPLICATIONS

This application claims priority to U.S. Provisional Patent Application Ser. No. 62/180,562, filed Jun. 16, 2015, the entire contents of which are incorporated herein by reference.

TECHNICAL FIELD

This disclosure generally relates to non-chemical methods of producing methionine or a methionine biosynthetic pathway-derived intermediates or a methionine-derived products.

BACKGROUND

Methionine is one of the most important essential amino acids in human and animal nutrition. It is the most limiting amino acid in poultry and the largest additive in feed. Demand for methionine has been increasing more rapidly compared to other aspartate-family amino acids (i.e., lysine and threonine) due to the rising consumption of meats in developing countries. The major producers are adding capacity to meet the increasing demand.

Methionine is currently produced by chemical methods that involve highly toxic petrochemical raw materials such as hydrogen cyanide (produced from natural gas and ammonia), acrolein (produced from propylene) and methyl mercaptan (produced from methanol and sulfur). Raw materials used in the chemical-based method require extensive environmental and safety considerations in the operations, and produce a significant amount of waste stream.

SUMMARY

Applicants discovered that specific genetic modifications to bacterial and yeast strains allow the resulting bacterial and yeast strains to produce methionine or one or more methionine biosynthetic pathway-derived intermediates. Based on this discovery provided herein are recombinant bacterial strains and recombinant yeast strains that can be used to produce methionine and/or biosynthetic pathway-derived intermediates, and methods of producing methionine and/or one or more methionine biosynthetic pathway-derived intermediates using one or more of these recombinant bacterial strains and/or recombinant yeast strains.

Provided herein are methods of synthesizing methionine or one or more methionine biosynthetic pathway-derived intermediates that include culturing a recombinant bacterial strain including a heterologous nucleic acid encoding at least one protein and/or including a nucleic acid encoding at least one inactivated endogenous protein in a culture medium under conditions sufficient to produce L-methionine or one or more methionine biosynthetic pathway-derived intermediates, where the culture medium includes: (a) methane, methanol, sugars, glycerol, or a combination thereof; and (b) a source of sulfur. In some embodiments of these methods, the recombinant bacterial strain is a recombinant strain of one of the following bacterial species: *Methylosinus sporium*, *Methylosinus trichosporium*, *Methylocystis parvus*, *Methylocystis echinoides*, *Methylocystis rosea*, *Methylocystis heyeri*, *Methylocystis hirsuta*, *Methylocella palustris*, *Methylocella silvestris*, *Methylocella tundrae*, *Methylocapsa acidiphila*, *Methylocapsa aurea*, *Methyloferula stellata*, *Methylomonas aurantiaca*, *Methylomonas fodinarum*, *Methylomonas methanica*, *Methylomonas scandinavica*, *Methylomonas rubra*, *Methylomonas koyamae*, *Methylomonas paludis*, *Methylobacter psychrophilus*, *Methylobacter tundripaludum*, *Methylobacter luteus*, *Methylobacter bovis*, *Methylobacter marinus*, *Methylobacter whittenburyi*, *Methylococcus capsulatus*, *Methylococcus capsulatus*, *Methylococcus thermophilus*, *Methylococcus mobilis*, *Methylomicrobium agile*, *Methylomicrobium album*, *Methylomicrobium pelagicum*, *Methylomicrobium buryatense*, *Methylomicrobium kenyense*, *Methylomicrobium japanense*, *Methylomicrobium alcaliphilum*, *Methylosphaera hansonii*, *Methylocaldum gracile*, *Methylocaldum szegediense*, *Methylocaldum tepidum*, *Methylosarcina fibrata*, *Methylosarcina quisquiliarum*, *Methylosarcina lacus*, *Methylothermus thermalis*, *Methylothermus subterraneus*, *Methylohalobius crimeensis*, *Methylogaea oryzae*, *Methylosoma difficile*, *Methylomarinum vadi*, *Methylovulum miyakonense*, *Crenothrix polyspora*, *Clonothrix fusca*, *Methylacidiphilum fumariolicum*, *Methylacidiphilum kamchatkensis*, and *Methylacidiphilum infernorum*.

In some embodiments of these methods, the recombinant bacterial strain is a recombinant strain of one of the following bacterial species: *Methylomicrobium buryatense* 5G, *Methylobacterium extorquens* AM1, *M. extorquens* ATCC 55366, *M. extorquens* DM4, *M. extorquens* CM4, *M. extorquens* PA1, *M. extorquens* BJ001, *M. radiotolerans*, *M. nodulans*, *Methylobacterium* spp. 4-46, *Bacillus methanolicus* MGA3, and *Bacillus methanolicus* PB1. In some embodiments of these methods, the recombinant bacterial strain is a recombinant strain of *Methylomicrobium buryatense* 5G.

In some embodiments of these methods, the recombinant bacterial strain includes nucleic acid encoding at least one protein selected from the group of: pyruvate carboxylase, phosphoenolpyruvate carboxylase, aspartase, aspartate transaminase, aspartate kinase, homoserine dehydrogenase, and methionine transporter. In some examples of these methods, the pyruvate carboxylase is from *C. glutamicum*. In some examples of these methods, the phosphoenolpyruvate carboxylase is from *Synechococcus* sp. or *M. thermoautotrophicus*. In some embodiments of these methods, the heterologous nucleic acid encoding one of the at least one protein is operably linked to a promoter.

In some embodiments of these methods, the at least one inactivated endogenous protein is a result of a deletion in an endogenous gene encoding one of the least one endogenous proteins. In some embodiments of these methods, the at least one inactivated endogenous protein is a result of a point mutation in an endogenous gene encoding one of the at least one endogenous proteins.

In some embodiments of these methods, the recombinant bacterial strain includes at least inactivated endogenous protein selected from the group of: lactate dehydrogenase, pyruvate formate lyase, methionine adenosyl transferase, phosphate acetyltransferase, starch synthase, oxaloacetate decarboxylase, malic enzyme, sucrose phosphate synthase, and ectoine synthase.

In some embodiments of these methods, the recombinant bacterial strain further includes heterologous nucleic acid encoding one or more of protein selected from the group consisting of: formaldehyde dehydrogenase, formate dehydrogenase, aspartokinase, aspartate-semialdehyde dehydrogenase, homoserine dehydrogenase, and methionine synthase. In some embodiments of these methods, the aspartate kinase is a feedback-resistant aspartate kinase. In some embodiments of these methods, the heterologous nucleic acid encoding one of the at least one protein selected from the group of: formaldehyde dehydrogenase, formate dehydrogenase, aspartokinase, aspartate-semialdehyde dehydrogenase, homoserine dehydrogenase, and methionine synthase, is operably linked to a promoter.

In some embodiments of these methods, the culture medium includes methanol or methane. In some embodiments of these methods, the culture medium includes methanol as the only carbon source. In some embodiments of these methods, the culture medium includes glucose and methanol. In some embodiments of these methods, the culture medium comprises glucose and the recombinant bacterial strain further includes a heterologous nucleic acid that encodes a glucose transporter. In some embodiments of these methods, the heterologous nucleic acid encoding the glucose transporter is operably linked to a promoter.

In some embodiments of these methods, the recombinant bacterial strain further includes a heterologous nucleic acid encoding the *Methylomicrobium buryatense* 5G pyrophosphate-dependent 6-phosphofructose kinase. In some embodiments of these methods, the heterologous nucleic acid encoding the *Methylomicrobium buryatense* 5G pyrophosphate-dependent 6-phosphofructose kinase is operably linked to a promoter.

Some embodiments of these methods further include harvesting methionine synthesized by the recombinant bacterial strain. Some embodiments of these methods further include harvesting a methionine biosynthetic pathway intermediate synthesized by the recombinant bacterial strain. In some embodiments of these methods, the methionine biosynthetic pathway intermediate is selected from the group of: oxaloacetate, aspartate, homoserine, O-succinyl-L-homoserine, O-acetyl-L-homoserine, cystathionine, and homocysteine.

Some embodiments of these methods further include harvesting an enzymatic product generated using methionine as a substrate, synthesized by the recombinant bacteria strain. In some embodiments of these method, the enzymatic product generated using methionine as a substrate is selected from the group of: S-adenosyl-methionine, and dipeptides that comprise methionine. In some embodiments of these methods, the recombinant bacterial strain further includes heterologous nucleic acid encoding a homoserine O-acetyltransferase, and the enzymatic product generated is O-acetyl-L-homoserine. In some embodiments of these methods, the heterologous nucleic acid encoding the homoserine O-acetyltransferase is operably linked to a promoter.

In some embodiments of these methods, the recombinant bacterial strain further includes heterologous nucleic acid encoding methionine adenosyl transferase, and the enzymatic product generated is S-adenosyl-methionine. In some embodiments of these methods, the nucleic acid encoding methionine adenosyl transferase is operably linked to a promoter. In some embodiments of these methods, the recombinant bacteria strain further includes heterologous nucleic acid encoding L-amino acid ligase, and the enzymatic product generated is a dipeptide that comprises methionine. In some examples of these methods, the heterologous nucleic acid encoding L-amino acid ligase is operably linked to a promoter.

In some embodiments of any of the methods described herein, the promoter is an inducible promoter or a constitutive promoter. In some embodiments of any of the methods described herein, the promoter is a heterologous promoter.

In some embodiments of these methods, the pyruvate carboxylase is a feedback-resistant pyruvate carboxylase. In some embodiments of any of the methods described herein, the culturing is performed under anaerobic conditions. In some embodiments of any of the methods described herein, the source of sulfur is selected from the group of: ammonium sulfate, sodium sulfate, magnesium sulfate, potassium sulfate, ammonium thiosulfate, methanethiol, and dimethylthiol.

Some embodiments of these methods further include adding the harvested methionine to an animal feed or food product. Some embodiments of these methods further include adding the harvested methionine biosynthetic pathway intermediate to an animal feed or food product. Some embodiments of these methods further include adding the harvested enzymatic product generated using methionine as a substrate to an animal feed or food product.

Also provided are recombinant bacterial strains that include heterologous nucleic acid encoding at least one protein and/or include nucleic acid encoding at least inactivated endogenous protein, that is capable of producing L-methionine or a methionine biosynthetic pathway-derived intermediate in a culture medium under conditions sufficient to produce L-methionine or a methionine biosynthetic pathway-derived intermediate, wherein the culture medium includes: (a) methane, methanol, sugars, glycerol, or a combination thereof; and (b) a source of sulfur. In some embodiments of these recombinant bacterial strains, the recombinant bacterial strain is a recombinant strain of one of the following bacterial species: *Methylosinus sporium, Methylosinus trichosporium, Methylocystis parvus, Methylocystis echinoides, Methylocystis rosea, Methylocystis heyeri, Methylocystis hirsuta, Methylocella palustris, Methylocella silvestris, Methylocella tundrae, Methylocapsa acidiphila, Methylocapsa aurea, Methyloferula stellata, Methylomonas aurantiaca, Methylomonas fodinarum, Methylomonas methanica, Methylomonas scandinavica, Methylomonas rubra, Methylomonas koyamae, Methylomonas paludis, Methylobacter psychrophilus, Methylobacter tundripaludum, Methylobacter luteus, Methylobacter bovis, Methylobacter marinus, Methylobacter whittenburyi, Methylococcus capsulatus, Methylococcus capsulatus, Methylococcus thermophilus, Methylococcus mobilis, Methylomicrobium agile, Methylomicrobium album, Methylomicrobium pelagicum, Methylomicrobium buryatense, Methylomicrobium kenyense, Methylomicrobium japanense, Methylomicrobium alcaliphilum, Methylosphaera hansonii, Methylocaldum gracile, Methylocaldum szegediense, Methylocaldum tepidum, Methylosarcina fibrata, Methylosarcina quisquiliarum, Methylosarcina lacus, Methylothermus thermalis, Methylothermus subterraneus, Methylohalobius crimeensis, Methylogaea oryzae, Methylosoma difficile, Methylomarinum vadi, Methylovulum miyakonense, Crenothrix polyspora, Clonothrix fusca, Methylacidiphilum fumariolicum, Methylacidiphilum kamchatkensis*, and *Methylacidiphilum infernorum*. In some embodiments of these recombinant bacterial strains, the recombinant bacterial strain is a recombinant strain of one of the following bacterial species: *Methylomicrobium buryatense* 5G, *Methylobacterium extorquens* AM1, *M. extorquens* ATCC 55366, *M. extorquens* DM4, *M. extorquens* CM4, *M. extorquens* PA1, *M. extorquens* BJ001, *M. radiotolerans, M. nodulans, Methylobacterium* spp. 4-46, *Bacillus methanolicus* MGA3, and *Bacillus methanolicus* PB1. In some embodiments of these recombinant bacterial strains, the recombinant bacterial strain is a recombinant strain of *Methylomicrobium buryatense* 5G.

In some examples of these recombinant bacterial strains, the recombinant bacterial strain includes nucleic acid encoding at least one protein selected from the group of: pyruvate carboxylase, phosphoenolpyruvate carboxylase, aspartate transaminase, aspartate kinase, homoserine dehydrogenase, and methionine transporter. In some examples of these recombinant bacterial strains, the pyruvate carboxylase is from *C. glutamicum*. In some embodiments of these recombinant bacterial strains, the phosphoenolpyruvate carboxylase is from *Synechococcus* sp. or *M. thermoautotrophicus*. In some examples of these recombinant bacterial strains, the heterologous nucleic acid encoding one of the at least one protein is operably linked to a promoter.

In some examples of these recombinant bacterial strains, the at least one inactivated endogenous protein is a result of a deletion in an endogenous gene encoding one of the least one endogenous proteins. In some embodiments of these recombinant bacterial strains, the at least one inactivated endogenous protein is a result of a point mutation in an endogenous gene encoding one of the at least one endogenous proteins. In some examples of these recombinant bacterial strains, the recombinant bacterial strain comprises at least inactivated endogenous protein selected from the group consisting of: lactate dehydrogenase, pyruvate formate lyase, methionine adenosyl transferase, phosphate acetyltransferase, starch synthase, oxaloacetate decarboxylase, malic enzyme, sucrose phosphate synthase, and ectoine synthase.

In some embodiments of these recombinant bacterial strains, the recombinant bacterial strain further includes heterologous nucleic acid encoding one or more of protein selected from the group of: formaldehyde dehydrogenase, formate dehydrogenase, aspartokinase, aspartate-semialdehyde dehydrogenase, homoserine dehydrogenase, and methionine synthase. In some embodiments of these recombinant bacterial strains, the aspartate kinase is a feedback-resistant aspartate kinase. In some embodiments of these recombinant bacterial strains, the heterologous nucleic acid encoding one of the at least one protein selected from the group of: formaldehyde dehydrogenase, formate dehydrogenase, aspartokinase, aspartate-semialdehyde dehydrogenase, homoserine dehydrogenase, and methionine synthase, is operably linked to a promoter.

In some embodiments of these recombinant bacterial strains, the recombinant bacterial strain further includes a heterologous nucleic acid that encodes a glucose transporter. In some embodiments of these recombinant bacterial strains, the heterologous nucleic acid encoding the glucose transporter is operably linked to a promoter.

In some embodiments of these recombinant bacterial strains, the recombinant bacterial strain further comprises a heterologous nucleic acid encoding the *Methylomicrobium buryatense* 5G pyrophosphate-dependent 6-phosphofructose kinase. In some examples of these recombinant bacterial strains, the heterologous nucleic acid encoding the *Methylomicrobium buryatense* 5G pyrophosphate-dependent 6-phosphofructose kinase is operably linked to a promoter.

In some embodiments of these recombinant bacterial strains, the methionine biosynthetic pathway intermediate is selected from the group of: oxaloacetate, aspartate, homoserine, O-succinyl-L-homoserine, O-acetyl-L-homoserine, cystathionine, and homocysteine.

In some examples of these recombinant bacterial strains, the recombinant bacterial strain further includes heterologous nucleic acid encoding a homoserine O-acetyltransferase, and the recombinant bacterial strain is capable of generating the enzymatic product that utilizes methionine as a substrate of O-acetyl-L-homoserine. In some embodiments of these recombinant bacterial strains, the heterologous nucleic acid encoding the homoserine O-acetyltransferase is operably linked to a promoter.

In some embodiments of these recombinant bacterial strains, the recombinant bacterial strain further includes heterologous nucleic acid encoding methionine adenosyl transferase, and the recombinant bacterial strain is capable of generating the enzymatic product that utilizes methionine as a substrate of S-adenosyl-methionine. In some examples of these recombinant bacterial strains, the nucleic acid encoding methionine adenosyl transferase is operably linked to a promoter.

In some embodiments of these recombinant bacterial strains, the recombinant bacteria strain further includes heterologous nucleic acid encoding L-amino acid ligase, and the recombinant bacterial strain is capable of generating the enzymatic product that utilizes methionine as a substrate of a dipeptide that includes methionine. In some examples of these recombinant bacterial strains, the heterologous nucleic acid encoding L-amino acid ligase is operably linked to a promoter.

In some examples of any of the recombinant bacterial strains described herein, the promoter is an inducible promoter or a constitutive promoter. In some examples of any of the recombinant bacterial strains described herein, the promoter is a heterologous promoter.

In some embodiments of these recombinant bacterial strains, the pyruvate carboxylase is a feedback-resistant pyruvate carboxylase.

Also provided herein are compositions that include any of the recombinant bacterial strains described herein. Also provided are kits that include any of the compositions that include any of the recombinant bacterial strains described herein.

Also provided are methods of synthesizing methionine or a methionine biosynthetic pathway-derived intermediate that include culturing a recombinant yeast strain including heterologous nucleic acid encoding at least one protein and/or comprises nucleic acid encoding at least inactivated endogenous protein in a culture medium under conditions sufficient to produce L-methionine or a methionine biosynthetic pathway-derived intermediate, wherein the culture medium includes: (a) methane, methanol, sugars, glycerol, or a combination thereof; and (b) a source of sulfur. In some embodiments of these methods, the recombinant yeast strain is a recombinant strain of one of the following yeast genera: *Pichia, Hansenula, Torulopsis, Candida,* and *Karwinskia*. In some examples of these methods, the recombinant yeast strain is a recombinant strain of the yeast genera *Pichia*. In some examples of these methods, the recombinant yeast strain is a recombinant strain of one of the following yeast species: *Pichia pastoris, Pichia stipitis, Pichia ohmeri, Pichia caribaea, Pichia guilliermondii Pichia ciferri, Pichia kluyveri,* and *Pichia pinus*. In some examples of these methods, the recombinant yeast strain is a recombinant strain of *Pichia pastoris*.

In some embodiments of these methods, the recombinant yeast strain includes nucleic acid encoding at least one protein selected from the group of: phosphoenolpyruvate carboxylase, aspartate transaminase, aspartase, aspartate kinase, homoserine dehydrogenase, cobalamin-dependent methionine synthase, and methionine transporter. In some examples of these methods, the phosphoenolpyruvate carboxylase is from *Synechococcus* sp. or *M. thermoautotrophicus*. In some examples of these methods, the heterologous nucleic acid encoding one of the at least one protein is operably linked to a promoter.

In some embodiments of these methods, the at least one inactivated endogenous protein is a result of a deletion in an endogenous gene encoding one of the least one endogenous proteins. In some examples of these methods, the at least one inactivated endogenous protein is a result of a point mutation in an endogenous gene encoding one of the at least one endogenous proteins. In some examples of these methods, the recombinant yeast strain includes at least inactivated endogenous protein selected from the group of: methionine adenosyl transferase, arabitol dehydrogenase, and pyruvate carboxylase.

In some embodiments of these methods, the recombinant yeast strain further includes heterologous nucleic acid encoding one or more of protein selected from the group consisting of: formaldehyde dehydrogenase, formate dehydrogenase, aspartokinase, aspartate-semialdehyde dehydrogenase, homoserine dehydrogenase, and methionine synthase. In some examples of these methods, the aspartate kinase is a feedback-resistant aspartate kinase. In some examples of these methods, the heterologous nucleic acid encoding one of the at least one protein selected from the group of: formaldehyde dehydrogenase, formate dehydrogenase, aspartokinase, aspartate-semialdehyde dehydrogenase, homoserine dehydrogenase, and methionine synthase, is operably linked to a promoter.

In some embodiments of these methods, the culture medium includes methanol. In some embodiments of these methods, the culture medium includes methanol as the only carbon source. In some embodiments of these methods, the culture medium includes glucose and methanol. In some embodiments of these methods, the culture medium includes glucose. In some embodiments of these methods, the culture medium includes glucose as the only carbon source.

In some embodiments of these methods, the recombinant yeast strain further includes a heterologous nucleic acid encoding the *Methylomicrobium buryatense* 5G pyrophosphate-dependent 6-phosphofructose kinase. In some examples, the heterologous nucleic acid encoding the *Methylomicrobium buryatense* 5G pyrophosphate-dependent 6-phosphofructose kinase is operably linked to a promoter.

Some examples of these methods further include harvesting methionine synthesized by the recombinant yeast strain. Some embodiments of these methods further include harvesting a methionine biosynthetic pathway intermediate synthesized by the recombinant yeast strain. In some examples of these methods, the methionine biosynthetic pathway intermediate is selected from the group of: oxaloacetate, aspartate, homoserine, O-succinyl-L-homoserine, O-acetyl-L-homoserine, cystathionine, and homocysteine.

Some embodiments of these methods further include harvesting an enzymatic product generated using methionine as a substrate, synthesized by the recombinant yeast strain. In some examples of these methods, the enzymatic product generated using methionine as a substrate is selected from the group of: S-adenosyl-methionine, and dipeptides that comprise methionine.

In some embodiments of these methods, the recombinant yeast strain further includes heterologous nucleic acid encoding a homoserine O-acetyltransferase, and the enzymatic product generated is O-acetyl-L-homoserine. In some examples of these methods, the heterologous nucleic acid encoding the homoserine O-acetyltransferase is operably linked to a promoter.

In some embodiments of these methods, the recombinant yeast strain further includes heterologous nucleic acid encoding methionine adenosyl transferase, and the enzymatic product generated is S-adenosyl-methionine. In some examples of these methods, the nucleic acid encoding methionine adenosyl transferase is operably linked to a promoter.

In some embodiments of these methods, the recombinant yeast strain further includes heterologous nucleic acid encoding L-amino acid ligase, and the enzymatic product generated is a dipeptide that comprises methionine. In some examples of these methods, the heterologous nucleic acid encoding L-amino acid ligase is operably linked to a promoter.

In any of the methods described herein, the promoter is an inducible promoter or a constitutive promoter. In any of the methods described herein, the promoter is a heterologous promoter.

In some embodiments of these methods, the recombinant yeast strain further includes nucleic acid encoding at least inactivated endogenous pyruvate decarboxylase and an inactivated endogenous arabitol dehydrogenase.

In some examples of any of the methods described herein, the source of sulfur is selected from the group of: ammonium sulfate, sodium sulfate, magnesium sulfate, potassium sulfate, ammonium thiosulfate, methanethiol, and dimethylthiol.

Some embodiments of these methods further include adding the harvested methionine to an animal feed or food product. Some embodiments of these methods further include adding the harvested methionine biosynthetic pathway intermediate to an animal feed or food product. Some examples of these methods further include adding the harvested enzymatic product generated using methionine as a substrate to an animal feed or food product.

Also provided herein are recombinant yeast strains that include heterologous nucleic acid encoding at least one protein and/or that include nucleic acid encoding at least inactivated endogenous protein in a culture medium under conditions sufficient to produce L-methionine or a methionine biosynthetic pathway-derived intermediate, where the culture medium includes: (a) methane, methanol, sugars, glycerol, or a combination thereof; and (b) a source of sulfur. In some examples of these recombinant yeast strains, the recombinant yeast strain is a recombinant strain of one of the following yeast genera: *Pichia, Hansenula, Torulopsis, Candida*, and *Karwinskia*. In some examples of these recombinant yeast strains, the recombinant yeast strain is a recombinant strain of the yeast genera *Pichia*. In some examples of these recombinant yeast strains, the recombinant yeast strain is a recombinant strain of one of the following yeast species: *Pichia pastoris, Pichia stipitis, Pichia ohmeri, Pichia caribaea, Pichia guilliermondii, Pichia ciferri, Pichia kluyveri*, and *Pichia pinus*. In some examples of these recombinant yeast strains, the recombinant yeast strain is a recombinant strain of *Pichia pastoris*.

In some embodiments of these recombinant yeast strains, the recombinant yeast strain includes nucleic acid encoding at least one protein selected from the group of: phosphoenolpyruvate carboxylase, aspartate transaminase, aspartate kinase, homoserine dehydrogenase, cobalamin-dependent methionine synthase, and methionine transporter. In some examples of these recombinant yeast strains, the phosphoenolpyruvate carboxylase is from *Synechococcus* sp. or *M. thermoautotrophicus*. In some examples of these recombinant yeast strains, the heterologous nucleic acid encoding one of the at least one protein is operably linked to a promoter.

In some embodiments of these recombinant yeast strains, the at least one inactivated endogenous protein is a result of a deletion in an endogenous gene encoding one of the least one endogenous proteins. In some examples of these recombinant yeast strains, the at least one inactivated endogenous protein is a result of a point mutation in an endogenous gene encoding one of the at least one endogenous proteins. In some embodiments of these recombinant yeast strains, the recombinant yeast strain includes at least inactivated endogenous protein selected from the group consisting of: methionine adenosyl transferase, arabitol dehydrogenase, and pyruvate carboxylase.

In some embodiments of these recombinant yeast strains, the recombinant yeast strain further includes heterologous nucleic acid encoding one or more of protein selected from the group of: formaldehyde dehydrogenase, formate dehydrogenase, aspartokinase, aspartate-semialdehyde dehydrogenase, homoserine dehydrogenase, and methionine synthase. In some embodiments of these recombinant yeast strains, the aspartate kinase is a feedback-resistant aspartate kinase. In some embodiments of these recombinant yeast strains, the heterologous nucleic acid encoding one of the at least one protein selected from the group of: formaldehyde dehydrogenase, formate dehydrogenase, aspartokinase, aspartate-semialdehyde dehydrogenase, homoserine dehydrogenase, and methionine synthase, is operably linked to a promoter.

In some embodiments of these recombinant yeast strains, the recombinant yeast strain further includes a heterologous nucleic acid encoding the *Methylomicrobium buryatense* 5G pyrophosphate-dependent 6-phosphofructose kinase. In some examples of these recombinant yeast strains, the heterologous nucleic acid encoding the *Methylomicrobium buryatense* 5G pyrophosphate-dependent 6-phosphofructose kinase is operably linked to a promoter.

In some examples of these recombinant yeast strains, the methionine biosynthetic pathway intermediate is selected from the group consisting of: oxaloacetate, aspartate, homoserine, O-succinyl-L-homoserine, O-acetyl-L-homoserine, cystathionine, and homocysteine.

In some embodiments of these recombinant yeast strains, the recombinant yeast strain further includes heterologous nucleic acid encoding a homoserine O-acetyltransferase, and the recombinant yeast strain is capable of generating an enzymatic product that utilizes methionine as a substrate of O-acetyl-L-homoserine. In some examples of these recombinant yeast strains, the heterologous nucleic acid encoding the homoserine O-acetyltransferase is operably linked to a promoter.

In some embodiments of these recombinant yeast strains, the recombinant yeast strain further includes heterologous nucleic acid encoding methionine adenosyl transferase, and the recombinant yeast strain is capable of generating an enzymatic product that utilizes methionine as a substrate of S-adenosyl-methionine. In some examples of these recombinant yeast strains the nucleic acid encoding methionine adenosyl transferase is operably linked to a promoter.

In some embodiments of these recombinant yeast strains, the recombinant yeast strain further includes heterologous nucleic acid encoding L-amino acid ligase, and the recombinant yeast strain is capable of generating an enzymatic product that utilizes methionine as a substrate of a dipeptide that comprises methionine. In some examples of these recombinant yeast strains, the heterologous nucleic acid encoding L-amino acid ligase is operably linked to a promoter.

In some examples of any of the recombinant yeast strains described herein, the promoter is an inducible promoter or a constitutive promoter. In some examples of any of the recombinant yeast strains described herein, the promoter is a heterologous promoter.

In some embodiments of these recombinant yeast strains, the recombinant yeast strain further includes nucleic acid encoding at least inactivated endogenous pyruvate decarboxylase and an inactivated endogenous arabitol dehydrogenase.

Also provided are compositions that include any of the recombinant yeast strains described herein. Also provided are kits that include any of the compositions including any of the recombinant yeast strains described herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
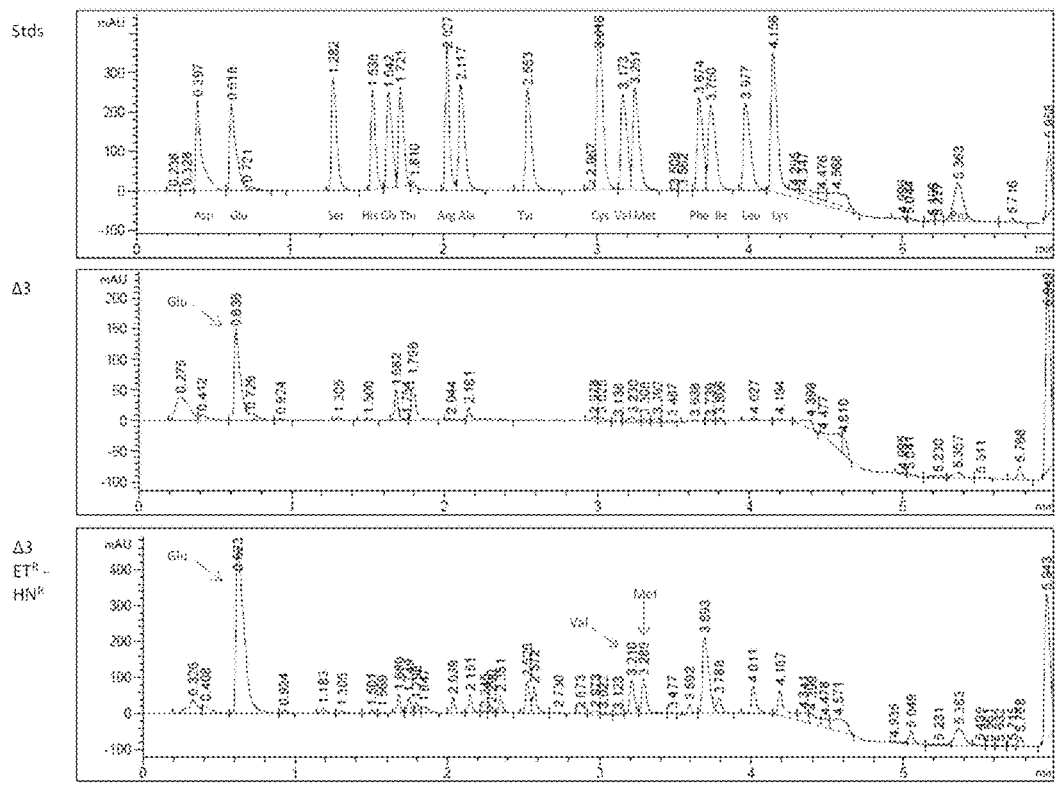
FIG. 1 shows the amino acid analysis by UHPLC 1290 affinity II (Agilent) in extracts isolated from MGC0966 selected on ethionine and MMS. Panel (A) shows the standard amino acid composition (100 pmol/µl); Panel (B) shows the amino acid composition from the MGC0966 strain; and Panel (C) shows the amino acid composition from the MGC0966 strain selected after growth in the presence of ethionine and hydroxy norvaline. The strains shown in Panels (B) and (C) were grown in minimal media containing 1% methanol for 3 days, and 3 ml of cells were used for extracting amino acids.

The high costs associated with methionine synthesis and the complex regulation of pathways involved in methionine synthesis have prevented the development of a commercial bioprocess for producing methionine. Although microorganisms that synthesize methionine from sugars have been generated, the yield of methionine in these strains has not been sufficient.

This disclosure provides for several different modified (e.g., recombinant) microorganisms (e.g., bacteria and yeast) that exhibit increased or optimized methionine production. As discussed herein, these modifications can include mutagenesis (e.g., random or targeted mutagenesis) of one or more endogenous nucleic acids and/or recombinant technology (e.g., introduction of one or more heterologous nucleic acids into the cell), and also can utilize selective pressure with amino acid analogs that deregulated methionine synthesis. As described herein, the pyruvate-phosphoenolpyruvate-oxaloacetate (PPO) node in different microorganisms can be engineered such that oxaloacetate is efficiently produced from pyruvate or phosphoenolpyruvate (PEP), and then converted to aspartate in the presence of glutamate and aspartate transaminase. The PPO node, which involves C3-carboxylation and C4-decarboxylation, plays an important role in the distribution of the carbon flux among catabolism, anabolism and energy supply, and organisms adjust flux through the PPO node based on the energetic and anabolic demands. The PPO node is able to act as a switch point for carbon flux distribution because it metabolically links glycolysis with the TCA cycle. While the central metabolic pathways is fairly conserved across microbial organisms, significant diversity exists at the PPO node. In some organisms, regulation of carbon flux at the PPO node is rather simple and straightforward. For example, in certain organisms, carbon catabolite repression ensures the absence of one or more C4-decarboxylating enzymes when glucose is present in sufficient quantity, and ensures the presence of this enzyme during growth on gluconeogenic substrates. However, in other organisms, regulation of carbon flux at the PPO node is complex, involving multiple carboxylating and decarboxylating enzymes that may be simultaneously active, even during growth on glucose as the sole carbon and energy source. Successful use of industrial strains for the production of lysine and other amino acids, therefore, requires a highly efficient PPO node, naturally occurring or engineered, that is able to channel carbon flux towards anabolism.

Microorganisms

Representative bacterial species that can be modified (e.g., made recombinant) as described herein include, without limitation, *Methylosinus sporium, Methylosinus trichosporium, Methylocystis parvus, Methylocystis echinoides, Methylocystis rosea, Methylocystis heyeri, Methylocystis hirsuta, Methylocella palustris, Methylocella silvestris, Methylocella tundrae, Methylocapsa acidiphila, Methylocapsa aurea, Methyloferula stellata, Methylomonas aurantiaca, Methylomonas fodinarum, Methylomonas methanica, Methylomonas scandinavica, Methylomonas rubra, Methylomonas koyamae, Methylomonas paludis, Methylobacter psychrophilus, Methylobacter tundripaludum, Methylobacter luteus, Methylobacter bovis, Methylobacter marinus, Methylobacter whittenburyi, Methylococcus capsulatus, Methylococcus capsulatus, Methylococcus thermophilus, Methylococcus mobilis, Methylomicrobium agile, Methylomicrobium album, Methylomicrobium pelagicum, Methylomicrobium buryatense* (e.g., *Methylomicrobium buryatense* 5G), *Methylobacterium extorquens* (e.g., *Methylobacterium extorquens* AM1, *M. extorquens* ATCC 55366, *M. extorquens* DM4, *M. extorquens* CM4, *M. extorquens* PA1, and *M. extorquens* BJ001), *Methylomicrobium kenyense, Methylomicrobium japanense, Methylomicrobium alcaliphilum, Methylosphaera hansonii, Methylocaldum gracile, Methylocaldum szegediense, Methylocaldum tepidum, Methylosarcina fibrata, Methylosarcina quisquiliarum, Methylosarcina lacus, Methylothermus thermalis, Methylothermus subterraneus, Methylohalobius crimeensis, Methylogaea oryzae, Methylosoma difficile, Methylomarinum vadi, Methylovulum miyakonense, Crenothrix polyspora, Clonothrix fusca, Methylacidiphilum fumariolicum, Methylacidiphilum kamchatkensis, Methylacidiphilum infernorum, M. radiotolerans, M. nodulans, Methylobacterium* spp. 4-46, and *Bacillus methanolicus* (*Bacillus methanolicus* MGA3, and *Bacillus methanolicus* PB1). Representative yeast genera that can be modified (e.g., made recombinant) as described herein include, without limitation, *Pichia, Hansenula, Torulopsis, Candida*, and *Karwinskia*. Simply by way of example, representative *Pichia* species include, without limitation, *Pichia pastoris, Pichia stipitis, Pichia ohmeri, Pichia caribaea, Pichia guilliermondii, Pichia ciferri, Pichia kluyveri*, and *Pichia pinus*.

Methods of inducing random mutagenesis in cells is known in the art. For example, random mutagenesis can be induced using a chemical mutagen, ionizing radiation, fast neutron bombardment, or combinations thereof. Representative chemical mutagens include, without limitation, nitrous acid, sodium azide, acridine orange, ethidium bromide, methyl methane sulfonate (MMS), and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of cell such that a mutation frequency is obtained that is below a threshold level characterized by lethality or reproductive sterility.

Similarly, selection or selective pressure also is well known and routinely used in the art. To obtain the modified or recombinant microorganisms described herein, selection on amino acid analogs can be used to deregulate methionine synthesis. Representative amino acid analogs include, without limitation, norleucine, α-methyl-methionine, ethionine, hydroxynorvaline, or combinations thereof.

Alternatively or additionally, one or more heterologous nucleic acids can be expressed (e.g., overexpressed) to produce a desired protein (e.g., an excess of a desired protein). As used herein, heterologous nucleic acid refers to any nucleic acid that is introduced (e.g., recombinantly) into the microorganism. For example, a heterologous nucleic acid can be a nucleic acid from a different genus or species, an additional (e.g., recombinant) copy of a nucleic acid sequence that already is present endogenously in the microorganism, or a codon-optimized nucleic acid. As used herein, a heterologous nucleic acid (e.g., a codon-optimized nucleic acid) can originate from any organism including, without limitation, fungi, bacteria, plants, or animals.

Representative proteins that can be produced by expressing (e.g., overexpressing) a heterologous nucleic acid include, for example, a phosphoenolpyruvate carboxylase, a pyruvate carboxylase, an aspartase, an aspartate transaminase, an aspartate kinase, a homoserine dehydrogenase, a cobalamin-dependent methionine synthase, and a methionine transporter. Simply by way of example, a cobalamin-dependent methionine synthase can be from an *E. coli* microorganism, *Corynebacterium* spp., the *M. buryatense* 5G microorganism, or many other bacterial species. In some embodiments, the heterologous nucleic acid encodes a pyrophosphate-dependent 6-phosphofructose kinase. A pyrophosphate-dependent 6-phosphofructose kinase can be derived from, for example, *Methylomicrobium buryatense* 5G. It would be appreciated that the protein encoded by the heterologous nucleic acid can be a feedback-resistant protein and, in some cases, it would be desirable for the protein encoded by the heterologous nucleic acid to be a feedback-resistant protein.

Phosphoenolpyruvate carboxylases catalyze the carboxylation of phosphoenolpyruvate into oxaloacetate and can be found, for example, in Accession No. NP_600799.1 GI: 19552797; Accession: EDV66579.1 GI: 190906978; Accession: BAA18393.1 GI: 1653480; Accession: EJG06574.1 GI: 395441817; Accession: Q5GM68.2 GI: 73917650;

Pyruvate carboxylases catalyze the carboxylation of pyruvate into oxaloacetate. Representative sequences of pyruvate carboxylases can be found, for example, in Accession No. NP_599921.1 (GI 19551919); Accession No. CAA71993.1 (GI 1871627); Accession No. CAB59603.1 (GI 6137048); Accession No. ETE99781.1 (GI 565336853); Accession No. BAP85874.1 (GI 716057916); Accession No. CAB59603.1 (GI 6137048).

Aspartases typically catalyze the reversible conversion of fumarate and ammonia into aspartate. The sequence of representative aspartases can be found, without limitation, in Accession No BAA00062.1 (GI 216859); Accession No. AAA23499.1 (GI 516605); Accession No. BAA04987.1 (GI: 1060862); Accession No. CAF21511.1 (GI 41325722); Accession No. NP_390238.2 (GI 255767512).

Aspartate transaminases typically catalyze conversion of glutamate and oxaloacetate into aspartate and ketoglutarate. The sequence of representative aspartate transaminases can be found, for example, in Accession No. EIJ83268.1 (GI 387590949); Accession No. NP_599493.1 (GI 19551491); Accession No. EDV67236.1 (GI 190907641); Accession No. AIU31792.1 (GI 698971982); Accession No. KHS50725.1 (GI 741030501); Accession No. WP_017840115.1 (GI 516451203).

Aspartate kinases typically catalyze conversion of aspartate into 4-phospho-L-aspartate. Representative aspartate kinase sequences include, without limitation, Accession No. ACX41573.1 (GI 260451151); Accession No. NP_599504.1 (GI 19551502); Accession No. KJJ41399.1 (GI 768926348); Accession No. CAY71375.1 (GI: 238033353); Accession No. WP_017839999.1 (GI 516451087); Accession No. WP_004436540.1 (GI: 490571520).

Homoserine dehydrogenases typically catalyze the conversion of aspartate-β-semialdehyde into homoserine. Representative homoserine dehydrogenase sequences can be found, for example, in Accession No. WP_017839313.1 (GI 516450401); Accession No. NP_600409.1 (GI 19552407); Accession No. AIE61203.1 (GI: 662719993); Accession No. CCA36962.1 (GI 328350562); Accession No. ABK59390.1 (GI 117958141).

Cobalamin-dependent methionine synthase is encoded by metH, which is present in many bacteria but is not present in *Pichia*. When expressed in yeast, the culture medium can be supplemented with cobalamin as necessary. Representative MetH sequences can be found, for example, in Accession No. CAE49788.1 (GI 38200108); Accession No. BAE78021.1 (GI: 85676771); Accession No. AIE60125.1 (GI 662718915); Accession No. WP_017842000.1 (GI 516453088); Accession No. WP_014147029.1 (GI 503913035).

Methionine transporter sequences can be found, for example, in Accession No. AAM46686.1 (GI 21311381); Accession No. AAM46685.1 (GI 21311380); Accession No. NP_417167.1 (GI 16130594); Accession No. NP 417168.1 (GI 16130595); Accession No. AHM72494 (GI 595640239); Accession No. AHM72493.1 (GI 595640238).

Pyrophosphate-dependent Phosphofructose kinases also are well known and representative sequences can be found, for example, in Accession No. Q3KSV5.1 (GI 122611506); Accession No. YP_004915565.1 (GI 357403641); Accession No. WP_017841163.1 (GI 516452251); Accession No. EIC28912.1 (GI 380883035).

Many enzymes can catalyze the carboxylation of PEP or the carboxylation of pyruvate to oxaloacetate or malate. These enzymes include pyruvate carboxylase, PEP carboxylase, PEP carboxykinase, PEP carboxytransphosphorylase, and malic enzyme. Although all of these enzymes can catalyze a carboxylation reaction, the anaplerotic carboxylation reaction is primarily mediated by either PEP carboxylase or pyruvate carboxylase. PEP carboxylase, which is present only in bacteria and plants, catalyzes the highly exergonic and irreversible bicarbonate fixation on PEP to form oxaloacetate. PEP carboxylase is usually a tetramer with each subunit having a mass of ~90-110 kDa. A much smaller PEP carboxylase (subunit size of 55 kDa) has been identified in *M. thermoautotrophicus*. In contrast to the PEP carboxylases from bacteria and plants, activity of an archaeal PEP carboxylase enzyme is not influenced by acetyl-CoA and is much less sensitive to aspartate.

Pyruvate carboxylase is a biotin-containing enzyme that catalyzes ATP-dependent irreversible carboxylation of pyruvate to oxaloacetate. In some organisms, the active enzyme consists of homotetramer, with each subunit having a mass of ~120-130 kDa. In some organisms, pyruvate carboxylase consists of different subunits (e.g., two different subunits, alpha and beta, forming a tetrameric enzyme, where the alpha subunit (~65 kDa) carries the biotin moiety and contains the catalytically active sites for the reaction, and the beta subunit (~55 kDa) is responsible for the conformational stability in the core of the enzyme). Regardless of the enzyme structure and composition, pyruvate carboxylase catalysis consists of two steps, i.e. the ATP-dependent carboxylation of the enzyme-bound biotin, and the transfer of the activated carboxyl group onto pyruvate. While most organisms contain PEP carboxylase, only a few bacteria use pyruvate carboxylase as the major enzyme in the anaplerotic carboxylation reaction. In some bacteria (e.g., *C. glutamicum*), both carboxylases are present. Activity of most pyruvate carboxylases are inhibited by aspartate, AMP, ADP, and 2-oxoglutarate; however, feedback-resistant forms of pyruvate carboxylase are known in the art.

PEP carboxykinase and malic enzyme can catalyze reversible C3-carboxylation/C4-decarboxylation reactions; however, they are primarily responsible for decarboxylation. PEP carboxykinase typically catalyzes the reversible decarboxylation of oxaloacetate to PEP, and malic enzymes typically catalyze the reversible decarboxylation of malate to pyruvate with simultaneous reduction of NAD. Many bacteria additionally possess an oxaloacetate decarboxylase, which catalyzes the irreversible decarboxylation of oxaloacetate to produce PEP.

Alternatively or additionally, one or more endogenous nucleic acids in the microorganism can be knocked-out, using, for example, mutation or deletion, such that an inactivated protein is produced or a microorganism that lacks the protein is produced. It would be appreciated that the mutation that results in an inactive protein can be a substitution, deletion, or insertion, or a mutation or a deletion can result in a truncated protein that lacks activity. Methods of targeted mutagenesis are known in the art, and include, for example, TALEN technologies (see, for example, Li et al., 2011, Nucleic Acids Res., 39(14):6315-25), zinc-finger technologies (see, for example, Wright et al., 2005, The Plant J., 44:693-705), and CRISPR technologies (see, for example, Mali et al., 2013, Nature Methods, 10:957-63).

The particular protein(s) inactivated in the microorganism depends upon a number of factors including, for example, the particular microorganism that is used as well as the amino acid that is being produced. In some embodiments, one or more genes involved in the production of fermentative waste products can be deleted or mutated in order to reduce the amount of one or more waste products or to shunt one or more of the waste products into one or more useful or productive pathways. For example, the endogenous protein that is inactivated in bacteria can be a lactate dehydrogenase, a pyruvate formate lyase, a methionine adenosyl transferase, a phosphate acetyltransferase, a starch synthase, an oxaloacetate decarboxylase, a malic enzyme, a sucrose phosphate synthase, and an ectoine synthase. In some embodiments, the endogenous protein that is inactivated in yeast can be an arabitol dehydrogenase, a methionine adenosyl transferase, and/or a pyruvate decarboxylase.

Nucleic acids are well known in the art, and can include DNA, RNA, and/or one or more nucleotide analogs or backbone modifications. A nucleic acid can be single stranded or double stranded, which usually depends upon its intended use. The nucleic acids provided herein typically encode proteins. While representative nucleic acids and proteins are provided herein, nucleic acids and proteins that differ from such sequences also are provided. Nucleic acids and proteins that differ in sequence from those provided herein can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to those sequences provided herein (e.g., in the form of a database accession number).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or protein sequences to be carried out across their entire length (global alignment). Chenna et al., 2003, Nucleic Acids Res., 31(13):3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of protein sequences, the following parameters can be used: word size: 1; window size: 5; scoring method: percentage; number of top diagonals: 5; and gap penalty: 3. For multiple alignment of protein sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

As discussed herein, modifications can be introduced into a nucleic acid, thereby leading to changes in the amino acid sequence of the encoded protein. For example, modifications can be introduced into nucleic acid coding sequences using mutagenesis (e.g., site-directed mutagenesis, PCR-mediated mutagenesis, random mutagenesis, TALEN, and/or CRISPR) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid is a nucleic acid that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid is generally introduced into a vector (e.g., a cloning vector, or an expression vector) for convenience of manipulation or to generate a recombinant molecule. In addition, an isolated nucleic acid molecule can include an engineered nucleic acid molecule such as a recombinant or a synthetic nucleic acid molecule.

As used herein, a "purified" protein is a protein that has been separated or purified from cellular components that naturally accompany it. Typically, the protein is considered "purified" when it is at least 70% (e.g., at least 75%, 80%, 85%, 90%, 95%, or 99%) by dry weight, free from the proteins and naturally occurring molecules with which it is naturally associated. Since a protein that is chemically synthesized is, by nature, separated from the components that naturally accompany it, a synthetic protein is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Proteins can be purified from natural sources (e.g., a biological sample) by known methods such as DEAE ion exchange, gel filtration, and hydroxyapatite chromatography. A protein also can be purified, for example, by expressing a nucleic acid in an expression vector. In addition, a purified protein can be obtained by chemical synthesis. The extent of purity of a protein can be measured using any appropriate method, e.g., column chromatography, polyacrylamide gel electrophoresis, or HPLC analysis.

A vector containing a nucleic acid (e.g., a nucleic acid that encodes a protein) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion protein (i.e., a protein operatively linked to a heterologous protein, which can be at either the N-terminus or C-terminus of the protein). Representative heterologous proteins are those that can be used in purification of the encoded protein (e.g., 6×His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, conjugation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Proteins can be detected using antibodies. Techniques for detecting proteins using antibodies include enzyme linked immunosorbent assays (ELISAs), Western blots, immunoprecipitations and immunofluorescence. An antibody can be polyclonal or monoclonal. An antibody having specific binding affinity for a protein can be generated using methods well known in the art. The antibody can be attached to a solid support such as a microtiter plate using methods known in the art. In the presence of a protein, an antibody-protein complex is formed.

Detection (e.g., of an amplification product, a hybridization complex, or a protein) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods of Using Modified or Recombinant Microorganisms

The modified or recombinant microorganisms described herein can be cultured in order to synthesize methionine or a methionine biosynthetic pathway-derived intermediate or a methionine-based product. As used herein, methionine biosynthetic pathway intermediates include, without limitation, oxaloacetate, aspartate, homoserine, O-succinyl-L-homoserine, O-acetyl-L-homoserine, cystathionine, and homocysteine. A methionine based product include, without limitation, S-adenosyl methionine, and dipeptides It would be appreciated by a skilled artisan that the conditions under which a microorganism is cultured will be dependent upon the particular background of the microorganism as well as the combination of endogenous and heterologous nucleic acids that are functionally expressed by the microorganism. It also would be appreciated by a skilled artisan that the synthesis of methionine or a methionine biosynthetic pathway-derived intermediate requires the presence of a source of sulfur in the medium. Representative sources of sulfur include, for example, ammonium sulfate, sodium sulfate, magnesium sulfate, potassium sulfate, ammonium thiosulfate, methanethiol, and dimethylthiol.

Depending on the particular modified or recombinant microorganism, the culturing step may be performed under anaerobic conditions. In some embodiments, the medium in which the modified or recombinant microorganism is cultured includes methanol, for use as a methyl donor, glucose, which will aid in the production of homocysteine, or both glucose and methanol. In some embodiments, methanol is the only carbon source; in some embodiments, glucose is the only carbon source. It would be understood by a skilled artisan that, when the culture medium includes glucose, the microorganism should express a nucleic acid that encodes a glucose transporter. Such a nucleic acid can be endogenous or heterologous to the microorganism.

Exemplary glucose transporter sequences can be found, without limitation, in Accession No. CAQ33253.1 (GI 242378469); Accession No. AAA27691.1 (GI 155590); Accession No. BAA10117.1 (GI 1001492); Accession No. P11166.2 (GI 115502394); Accession No. Q9P3U6 (GI 12230093); Accession No. P23585.1 (GI 12390); Accession No. A6ZT02.1 (GI 29046332).

The modified or recombinant microorganisms described herein, which synthesize methionine or a methionine biosynthetic pathway-derived intermediate, also can be used to produce an enzymatic product that is generated using methionine as a substrate. Simply by way of example, enzymatic products that can be generated using methionine as a substrate include S-adenosyl-methionine, and dipeptides that comprise methionine. In some embodiments, a modified microorganism as described herein also can include a heterologous nucleic acid encoding a homoserine O-acetyltransferase, such that O-acetyl-L-homoserine is generated as an enzymatic product. In some embodiments, a modified microorganism as described herein also can include a heterologous nucleic acid encoding methionine adenosyl transferase, such that S-adenosyl-methionine is generated as an enzymatic product. In some embodiments, a modified microorganism as described herein also can include a heterologous nucleic acid encoding L-amino acid ligase, such that a dipeptide that includes methionine is generated as an enzymatic product.

Simply by way of example, representative sequences for L-amino acid ligases can be found, for example, in Accession No. AAM90571.1 (GI 22085769); Accession No. KFX84640.1 (GI 682151323); Accession No. AAU25674.1 (GI 52005732); Accession No. BAG72134.1 (GI 207367328); Accession No. BAJ15424.1 (GI 304434482).

After a modified or recombinant microorganism as described herein has been cultured and the methionine or methionine biosynthetic pathway intermediate has been synthesized, the methionine or methionine biosynthetic pathway intermediate can be harvested. In embodiments in which an enzymatic product is generated using methionine or a methionine biosynthetic pathway intermediate as a substrate, the enzymatic product can be harvested.

It would be appreciated by a skilled artisan that the methionine, the methionine biosynthetic pathway intermediate, or the enzymatic product generated using methionine as a substrate that is harvested from a culture of the modified microorganism can be added to an animal feed or food product in a suitable amount. A suitable amount of methionine, a methionine biosynthetic pathway intermediate, or an enzymatic product generated using methionine as a substrate will be dependent on the particular animal food or food product and its intended use.

Methods of Generating a Recombinant Bacterium or Recombinant Yeast Cell Capable of Synthesizing Methionine or a Methionine Biosynthetic Pathway-Derived Intermediate Also provided herein are methods of generating a recombinant bacterium (e.g., any of the recombinant bacterial strains described herein) or recombinant yeast cell (e.g., any of the recombinant yeast strains described herein). These methods include introducing heterologous nucleic acid encoding at least one protein (e.g., any combination of one or more protein(s) described herein) and/or mutagenizing the recombinant bacterium or recombinant yeast cell in order to result in endogenous nucleic acid encoding at least one inactivated endogenous protein (e.g., any combination of the one or more inactivated endogenous protein(s) described herein). For example, the mutagenizing can be performed using chemical mutagenesis or targeted mutagenesis (e.g., using biotechnology techniques). An inactivated protein can include one or more point mutation(s) (e.g., one or more amino acid deletion(s), one or more amino acid substitution(s), and/or one or more amino acid insertion(s)) that results in inactivation of the protein. An inactivated protein can have a truncation (e.g., an N- and/or C-terminal truncation) that leads to inactivation of the protein. An inactivated protein can also have a deletion of one or more amino acids from an internal sequence within the protein. An inactivated protein can also be caused by a deletion of a nucleic acid encoding the protein (e.g., a complete deletion of the endogenous nucleic acid encoding the protein).

These methods can further include testing whether the recombinant bacterium or the recombinant yeast produces methionine or a methionine biosynthetic pathway-derived intermediate (e.g., using any of the methods described herein or known in the art).

The resulting recombinant bacterium or the resulting recombinant yeast can be used to produce methionine or a methionine biosynthetic pathway-derived intermediate (e.g., using any of the methods described herein or known in the art).

Compositions and Kits

This disclosure also provides for compositions and kits (e.g., articles of manufacture) containing one or more of the modified or recombinant microorganisms described herein. A composition or kit provided herein can include, in addition to one or more of the modified or recombinant microorganisms described herein, one or more components for culturing the modified or recombinant microorganism (e.g., one or more co-factors, nutrients, minerals, buffers, enzymes, substrates (e.g., a sulfur substrate) and/or a carbon source), and also can include suitable packaging materials. Suitable packaging materials can include instructions for culturing and/or using the one or more modified or recombinant microorganisms to produce one or more amino acids.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Generation of *Methylomicrobium buryatense* Strains Over-Producing Methionine Methionine synthesis is highly regulated by feedback regulation at a number of steps. To eliminate some of these feedback regulations, selection pressure and mutagenesis was used to generate a new recombinant *M. buryatense* 5G strain, named MGC0966. The methods that were used to generate this strain is described in Example 8. Briefly, three genes encoding pyruvate formate lyase (pfl), lactate dehydrogenase (ldh), and phosphate acetyltransferase (pta) were deleted in the wild type 5G strain resulting in generation of MGC0966 strain. Briefly, the 5G strain was mutagenized with methyl methanesulfonate and then cells plated on solid plates containing 1.5% agar in the presence of 1 mM ethionine and 10 mM hydroxy norvaline. Plates were incubated in air-tight jar containing methane:air at 1:1. After ~5 days, multiple colonies were obtained and re-streaked again on plates containing the same media under the same conditions. Eighteen colonies were selected and grown in liquid media in the presence of 1% methanol. The initial screening for a best methionine producing strains was performed by spectrophotometric analysis. Once the best performing strain was selected, the amino acid profile was determined using UHPLC following fermentation. The results are shown in FIG. 1. As can be seen, the three prominent amino acids present in the selected strain was glutamate, valine and methionine. While glutamate also is present in the original 5G strain, valine and methionine were present only in the selected MGC0966 strain.

Example 2—Additional Genetic Modification

Additional genes modification are made to further channel the carbon flux towards methionine production. This includes deleting the formate dehydrogenase gene, reducing the expression of the essential genes involved in lysine and threonine synthesis, and channeling pyruvate towards the synthesis of aspartate.

Example 3—Optimization of the Oxaloacetate Production

The objective herein is to optimize the PPO node in *M. buryatense* 5G for conversion of methane/methanol into methionine. The preliminary work with the metabolic engineering of *M. buryatense* 5G has shown significant improvement in the production of methionine. Measurement of amino acids in the optimized strain using UHPLC have shown that, in addition to methionine, a significant amount of valine and glutamate also is produced. This suggests that pyruvate is converted into valine, and indicates a significant block in the conversion of glutamate into aspartate due to inefficient carboxylation of pyruvate and/or conversion of PEP into oxaloacetate. It was therefore hypothesized that efficient conversion of glutamate into aspartate would further increase the methionine production. Optimization of the PPO node leading to increased synthesis of oxaloacetate is accomplished by overexpression of either pyruvate carboxylase or PEP carboxylase or both. This optimization allows significant improvement in methionine production in the recombinant strain. Therefore, the technical objectives are increasing the carboxylation of pyruvate and PEP and overexpressing aspartate transaminase.

Example 4—Expression of Pyruvate Carboxylase from *C. glutamicum*

The codon optimized pyc gene encoding pyruvate carboxylase from *C. glutamicum* is expressed in *M. buryatense* 5G strain using the expression system that utilizes a strong constitutive promoter.

Although many pyruvate carboxylase with varying enzyme kinetics from a number of different organisms have been characterized, *C. glutamicum* was selected as the source for the pyc gene used herein because it has very high specific activity, and because this enzyme is involved in ~90% of the carbon flux in *C. glutamicum* during anabolic reactions. The feedback-resistant form of this gene is used such that its activity is not affected by any metabolites. The presence of the pyc gene is confirmed in the engineered strain by PCR using genomic DNA and by measuring pyc steady state transcript levels by RT-PCR. Finally, pyruvate carboxylase activity is established using assays essentially as described in Peters-Wendisch et al., *Microbiol.* 144:915-927, 1998. After functional expression of pyruvate carboxylase has been established, its effectiveness in producing aspartate and glutamate is determined by comparing the amino acid profile in the parent and in the engineered strains using UHPLC. Functional expression of pyruvate carboxylase leads to higher carbon flux through aspartate (or other downstream products) and simultaneously reduces the accumulation of glutamate.

Example 5—Expression of PEP Carboxylase from *Synechococcus* sp

The codon optimized ppc gene encoding PEP carboxylase from photosynthetic bacterium is expressed in the *M. buryatense* 5G strain using the expression system described herein. Similar to the pyc gene, there is significant diversity in PEPC activity. Various PEPC enzymes from multiple sources were compared with respect to Km and Vmax for PEP, bicarbonate and magnesium. This analysis demonstrated that the PEPC enzyme from *Synechococcus* sp. is the best candidate enzyme. After expression of the ppc gene is established as described above, its effectiveness in channeling carbon flux towards aspartate is determined as described above. Functional expression of PEP carboxylase leads to higher accumulation of aspartate (or other downstream enzymes) and reduces accumulation of glutamate.

Example 6—Expression of PEP Carboxylase from *M. thermoautotrophicus*

Both pyruvate carboxylase and PEP carboxylase described above are large enzymes; for example, each active enzyme is ~440 kDa. In contrast to these, the PEP carboxylase from *M. thermoautotrophicus* is much smaller. The codon optimized ppc gene encoding the PEP carboxylase from *M. thermoautotrophicus* is expressed in the *M. buryatense* 5G strain using the expression system described above. Since this enzyme is not feedback-regulated by aspartate or other metabolites, the wild type gene is expressed in the *M. buryatense* 5G strain. After expression of the ppc gene is established as described herein, its effectiveness in C3 carboxylation is determined.

One of the risks associated with this enzyme is related to high temperature growth of the native organism. It is quite possible that optimum activity of this enzyme is achieved at high temperature. To determine the effect of various temperatures on the PEP carboxylase expressed in the *M. buryatense* 5G strain, its activity is determined at different temperatures. A high activity at 30° C. is desired.

Example 7—Combined Expression of Both C3-Carboxylating Enzymes

Based on the screening of genes for C3 carboxylation, it is expected that both enzymes, pyruvate and PEP carboxylating enzymes, are required for production of oxaloacetate, although it is possible that either pyruvate or PEP carboxylase will be sufficient. An optimized *M. buryatense* 5G strain ultimately is produced that efficiently channels carbon flux from methane/methanol towards methionine.

Example 8—Reduction or Elimination of Waste Products

Figure 2:
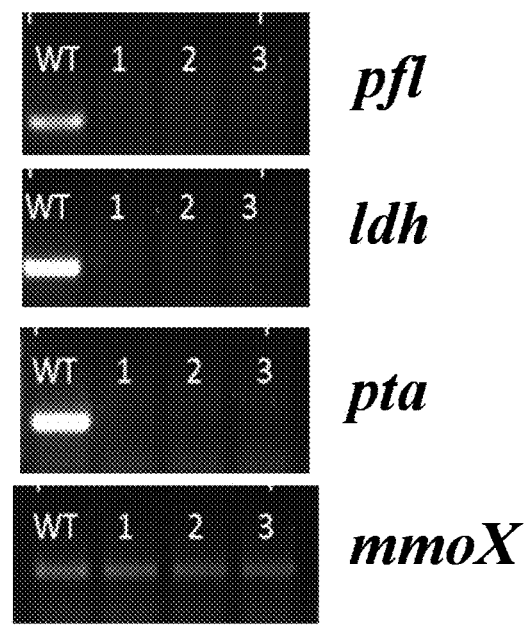
FIG. 2 photographs showing RT-PCR analysis of three independent lines of an *M. buryatense* 5G strain lacking the pfl, ldh, and pta genes. These genes were sequentially deleted and, after deletion of third gene, total RNA was isolated from wild type and from the three mutant strains. First strand synthesis was performed and the amount of transcript was determined using gene specific primers. Transcripts corresponding to mmoX were used as the control.

Similar to other industrial organisms, fermentation of methane/methanol by *M. buryatense* 5G strain leads to production of many waste products including lactate, acetate, and hydrogen. We, therefore, engineered a *M. buryatense* 5G strain in which production of lactate, acetate and other fermentative waste products were eliminated. Genes encoding pyruvate formate lyase (pfl), which catalyzes the conversion of pyruvate and co-enzyme A into formate and acetyl-CoA, lactate dehydrogenase (ldh), which catalyzes the conversion of pyruvate to lactate, and phosphate acetyltransferase (pta), which catalyzes the conversion of acetyl-CoA to CoA and acetyl phosphate, have been sequentially deleted. The absence of the respective genes was confirmed by PCR amplification using genomic DNA isolated from mutant strains. RT-PCR analysis of the three independent mutant strains shows that steady state transcript level of all three genes were absent, suggesting absence of these genes (FIG. 2). The resulting strain, hereafter MGC0966, missing these three genes have been used for optimization of methionine production.

Example 9—Methods of Producing L-Methionine Using the Recombinant *Methylomicrobium buryatense* 5G Strains Recombinant *Methylomicrobium buryatense* 5G strains described herein are used to produce L-methionine, or one or more methionine biosynthetic pathway-derived intermediates or one or more of L-methionine based products. The recombinant microorganisms are grown in a culture medium under conditions in which all modified enzymes including, but limited to, those that were inactivated or those that were overexpressed are working as intended and as described herein. The recombinant microorganisms are grown in a fermentor at a defined temperature(s) for a desired period of time. The recombinant microorganisms that are cultured can include other recombinant genes, such as genes for conversion of L-methionine into S-adenosyl methionine and dipeptide (which are present and expressed). The levels of substrates, intermediates, and/or final products are determined by extracting samples from the culture media for analysis.

A number of different liquid media can be used for growing recombinant *Methylomicrobium buryatense* 5G organisms in order to produce products such as L-methionine. The recombinant *Methylomicrobium buryatense* 5G cells can be, e.g., grown in shake flasks with constant shaking (150 rpm) in a minimal medium containing 0.2 g/L MgSO4.7H2O, 0.02 g/L CaCl2.6H2O, 1 g/L KNO3, and 7.5 g/L NaCl, as 94 well as 1× trace elements. 500× trace elements contains 1.0 g/L Na2-EDTA, 2.0 g/L 95 FeSO4.7H2O, 0.8 g/L ZnSO4.7H2O, 0.03 g/L MnCl2.4H2O, 0.03 g/L H3BO3, 0.2 g/L 96 CoCl2.6H2O, 0.6 g/L CuCl2.2H2O, 0.02 g/L NiCl2.6H2O, 0.05 g/L Na2MoO4.2H2O, 50 mM sodium carbonate buffer pH 9.5 and 2.3 mM phosphate buffer pH 6.8.

The recombinant microorganisms can be grown in fermentation vessels at a temperature of about 30° C. Once the cells are in the logarithmic phase, a substrate, e.g., methane, methanol, glycerol, glucose, or a combination of thereof, is fed into the vessel, the vessel is sealed air-tight, and cell growth is continued under the same culture conditions. The amount of substrate(s) converted into L-methionine or other product is/are determined by measuring the cell density at various times during culture.

The recombinant microorganism can be grown in a fed batch or continuous process (e.g., perfusion culture). In the perfusion culturing, the methane or methanol can be fed into the vessel after cells have reached logarithmic phase, at a rate constant at which the cells are able to convert the substrate into intermediates and to produce the final L-methionine product.

Example 10—Methods of Producing L-Methionine by the Recombinant *Pichia pastoris* Strains Recombinant *Pichia pastoris* strains described herein are cultured to produce L-methionine, one or more methionine biosynthetic pathway-derived intermediates, or one or more of L-methionine based products. The cell culturing and harvesting of L-methionine or other related products can be performed in shake flasks or in fermentors under similar conditions as described in Example 9.

As *Pichia pastoris* is a different kind of microorganism, it can be appreciated that it may a different liquid media than those described in Example 9. A number of different liquid media can be used for culturing recombinant *Pichia pastoris* organisms in order to produce products such as L-methionine. For example, recombinant *Pichia pastoris* cells can be grown in shake flasks with constant shaking (150 rpm) in a minimal medium containing a defined carbon source including glycerol, glucose, methanol, or a combination of these, 0.9 g/l citric acid monohydrate, 12.6 g/L $(NH_4)_2HPO_4$, 0.5 g/L $MgSO_4.7H_2O$, 1.5 g/L $KH_2PO_4$, 0.02 g/L $CaCl_2.2H_2O$, 5 ml/l trace salt solution, 2 mL/L Biotin solution (0.2 g/L). Variations of this exemplary media composition can be used to culture the recombinant *Pichia pastoris* strain and produce L-methionine, without affecting the yield, titer or rate of L-methionine production.

Example 11—Metabolic Engineering of *M. buryatense*

Three different recombinant *M. buryatense* strains were generated. The first strain is MGC0970 which includes deletions of the following three genes: formate lyase (pfl), lactate dehydrogenase (ldh), and phosphate acetyl transferase (pta). The second strain is MGC1122 which includes deletions of the following four genes: formate lyase (pdf), lactate dehydrogenase (ldh), phosphate acetyl transferase (pta), and diaminopimelate decarboxylase (lysA). The third strain is MGC1277 which includes deletions in formate lysate (pfl), lactate dehydrogenase (ldh), phosphate acetyl transferase (pta), and diaminopimelate decarboxylase (lysA), and the expression of two heterologous genes: a phosphoenolpyruvate carboxylase from *M. thermoautotrophicus* and a feedback resistant form of aspartate kinase from *C. glutamicum*.

Figure 3:
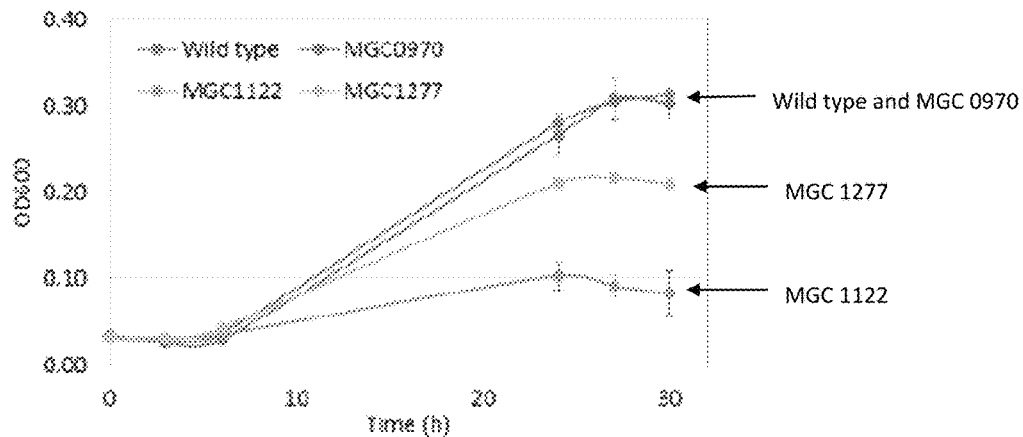
FIG. 3 is a graph showing the growth of the wild type strain, the MGC0970 strain, the MGC1122 strain, and the MGC1277 strain in NMS2 media. The mean data from three experiments is shown.
Figure 4:
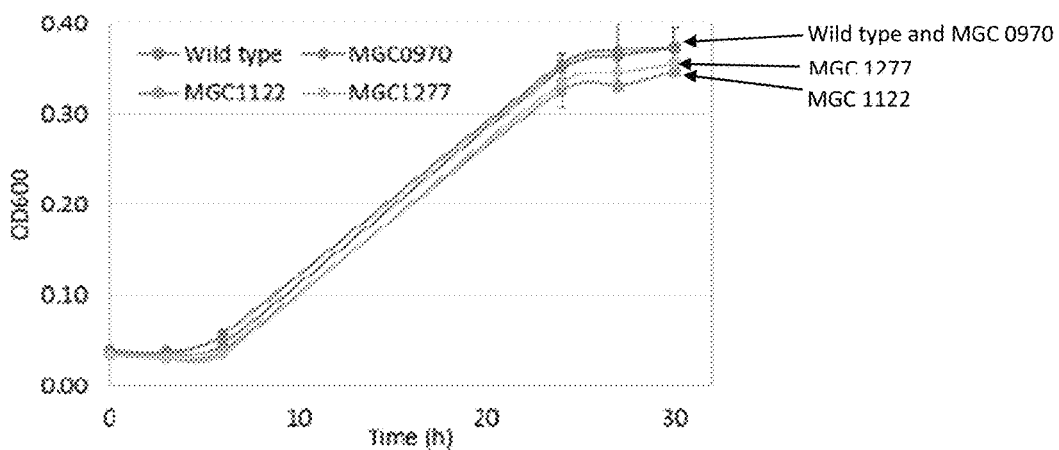
FIG. 4 is a graph showing the growth of the wild type strain, the MGC0970 strain, the MGC1122 strain, and the MGC1277 strain in NMS2 media supplemented with 0.01% yeast extract over time. The mean data from three experiments is shown.

The growth of the MGC0970, MGC1122, and MGC1277 strains was measured in NMS2 media including 0.2% methane in the absence or presence of 0.01% yeast extract (FIG. 3 and FIG. 4). MGC1122 and MGC1277 grew poorly when grown in minimal medium (FIG. 3), while the growth rate was recovered when 0.01% yeast extract was added to the medium (FIG. 4).

Figure 5:
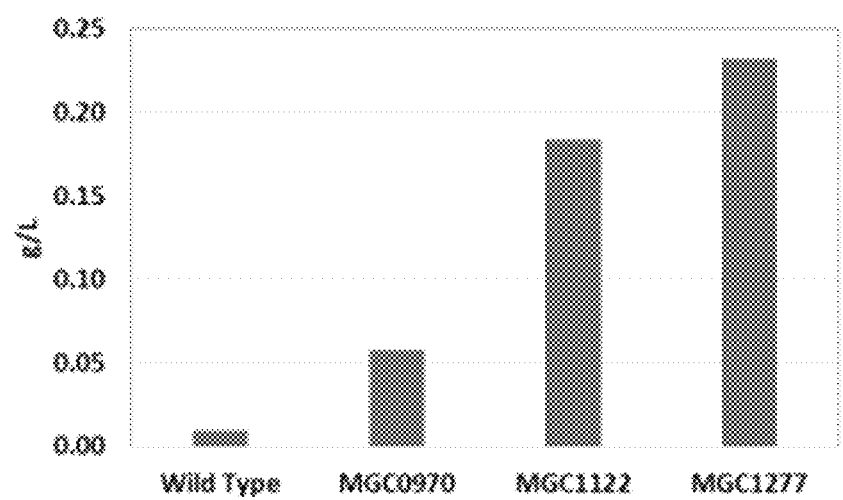
FIG. 5 is a graph showing the methionine production by the wild type strain, the MGC0970 strain, the MGC1122 strain, and the MGC1277 strain over time when cultured as described in Example 11.

Met production was measured in the wild type, MGC 0966, MGC 1122, and MGC1277 strains by UPLC (1290 Infinity II, Agilent) in shake flask under aerobic fermentation conditions. Cells were grown in 20 mL NMS2 media including 1% methanol. Additional methanol (2%) and potassium nitrate (10 mM) was added after 24 and 48 hours. At 72 hours, when cells had reached stationary phase, the following were added: 5% methanol, 50 mM sodium thiosulfate, 50 mM potassium nitrate, 80 μM biotin, 0.1 mM folic acid, and 50 μM vitamin B12. Fermentation was carried out for 24 hours. 5 mL of each culture was collected and free amino acids were isolated using methanol:chloroform method, and analyzed by UPLC. The data in FIG. 5 show that the MGC 0970 strain produces methionine, and the strain with an additional deletion of diaminopimelate decarboxylase (MGC1122) further improved methionine production. The data also show that the further heterologous expression of feedback genes of Met biosynthetic pathway in MGC 1122 further increased methionine production in this strain. MGC 1277 was the best performing strain: a titer of methionine of 0.23 g/L and a production rate of 0.01 g/L/hour was achieved with the MGC 1277 strain in this experiment.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of synthesizing methionine, the method comprising culturing a methanotrophic recombinant *Methylomicrobium buryatense* comprising nucleic acids encoding inactivated endogenous proteins of pyruvate formate lyase, lactate dehydrogenase, and phosphate acetyltransferase, in a culture medium under conditions sufficient to produce methionine, in a culture medium comprising:
    (a) methane, methanol, sugars, glycerol, or a combination thereof; and
    (b) a source of sulfur.

2. The method of claim 1, further comprising harvesting methionine synthesized by the methanotrophic recombinant *Methylomicrobium buryatense*.

3. The method of claim 2, further comprising adding the harvested methionine to an animal feed or food product.

4. The method of claim 1, wherein the methanotrophic recombinant *Methylomicrobium buryatense* further comprises:
    heterologous nucleic acid encoding at least one protein selected from the group consisting of: pyruvate carboxylase, phosphoenolpyruvate carboxylase, aspartate transaminase, aspartate kinase, homoserine dehydrogenase, and methionine transporter; and/or
    at least one additional inactivated endogenous protein selected from the group consisting of: methionine adenosyl transferase, diaminopimelate decarboxylase, starch synthase, oxaloacetate dehydrogenase, malic enzyme, sucrose phosphate synthase, and ectoine synthase.

5. The method of claim 1, wherein the methanotrophic recombinant *Methylomicrobium buryatense* further comprises:
    heterologous nucleic acid encoding one or more of protein selected from the group consisting of: formaldehyde dehydrogenase, formate dehydrogenase, aspartokinase, aspartate-semialdehyde dehydrogenase, homoserine dehydrogenase, and methionine synthase;
    a heterologous nucleic acid that encodes a glucose transporter;
    a heterologous nucleic acid encoding a homoserine O-acetyltransferase; and/or
    a heterologous nucleic acid encoding methionine adenosyl transferase.

6. The method of claim 4, wherein the pyruvate carboxylase is from *C. glutamicum*.

7. The method of claim 4, wherein the phosphoenolpyruvate carboxylase is from *Synechococcus* sp. or *M. thermoautotrophicus*.

8. The method of claim 1, wherein the methanotrophic recombinant *Methylomicrobium buryatense* is a recombinant *Methylomicrobium buryatense* 5G.

9. The method of claim 1, wherein at least one of the inactivated endogenous proteins is a result of a deletion in an endogenous gene encoding the endogenous protein.

10. The method of claim 1, wherein at least one of the inactivated endogenous proteins is a result of a point mutation in an endogenous gene encoding the endogenous protein.

11. The method of claim 4, wherein the aspartate kinase is a feedback-resistant aspartate kinase.

12. The method of claim 1, wherein the culture medium comprises methanol or methane.

13. The method of claim 1, wherein the culture medium comprises methanol as the only carbon source.

14. The method of claim 1, wherein the culture medium comprises glucose and methanol.

15. The method of claim 4, wherein the pyruvate carboxylase is a feedback-resistant pyruvate carboxylase.

16. The method of claim 1, wherein the culturing is performed under anaerobic conditions.

17. The method of claim 1, wherein the source of sulfur is selected from the group of: ammonium sulfate, sodium sulfate, magnesium sulfate, potassium sulfate, ammonium thiosulfate, methanethiol, and dimethylthiol.

18. The method of claim 1, wherein the methanotrophic recombinant *Methylomicrobium buryatense* further comprises inactivated endogenous diaminopimelate decarboxylase protein.

19. The method of claim 1, wherein the methanotrophic recombinant bacterial *Methylomicrobium buryatense* further comprises:
- heterologous nucleic acid encoding phosphoenolpyruvate carboxylase protein;
- heterologous nucleic acid encoding feedback-resistant form of aspartate kinase protein; and
- inactivated endogenous diaminopimelate decarboxylase protein.

* * * * *